United States Patent [19]

Butler et al.

[11] Patent Number: 4,782,071

[45] Date of Patent: Nov. 1, 1988

[54] TETRASUBSTITUTED UREA CHOLINERGIC AGENTS

[75] Inventors: Donald E. Butler, Holland; David M. Lustgarten, Ann Arbor; Walter H. Moos, Ann Arbor; Anthony J. Thomas, Ann Arbor, all of Mich.

[73] Assignee: Warner-Lambert Company, Morris Plains, N.J.

[21] Appl. No.: 926,163

[22] Filed: Nov. 3, 1986

[51] Int. Cl.$^4$ ............... A01N 43/40; C07D 239/02
[52] U.S. Cl. .................... 514/353; 514/352; 546/309; 546/255; 546/257; 544/360; 544/390
[58] Field of Search ............. 546/309; 514/352, 353

[56] References Cited

U.S. PATENT DOCUMENTS

| | | | |
|---|---|---|---|
| 3,904,602 | 9/1975 | Somlo | 260/239 E |
| 4,058,392 | 11/1977 | Thomas et al. | 71/106 |
| 4,083,814 | 4/1978 | Mark et al. | 260/30.8 R |
| 4,088,653 | 5/1978 | Knaus et al. | 260/295 AM |
| 4,349,526 | 9/1982 | Goor et al. | 423/588 |
| 4,425,208 | 1/1984 | Jacobine | 204/159.15 |
| 4,428,923 | 1/1984 | Kunkel et al. | 423/588 |
| 4,444,863 | 4/1984 | Sano et al. | 430/83 |
| 4,446,247 | 5/1984 | Jacobine | 502/167 |
| 4,472,583 | 9/1984 | Clifford | 546/309 X |
| 4,473,579 | 9/1984 | Devries et al. | 424/282 |
| 4,518,473 | 5/1985 | Jacobine | 204/159.15 |
| 4,551,562 | 11/1985 | Drauz et al. | 568/771 |
| 4,564,514 | 1/1986 | Drauz et al. | 423/589 |
| 4,628,126 | 12/1986 | Drauz et al. | 568/771 |
| 4,694,004 | 9/1987 | Nakaguti et al. | 546/309 X |

FOREIGN PATENT DOCUMENTS 1243591 1/1969 United Kingdom .

OTHER PUBLICATIONS

Chappelow, C. C. et al., *J. Chem. Eng. Data* 11 (3), pp. 436–442 (1966).

*Primary Examiner*—Teddy S. Gron
*Assistant Examiner*—Virginia B. Caress
*Attorney, Agent, or Firm*—Ronald A. Daignault

[57] ABSTRACT

Certain tetrasubstituted alkyl, aryl, pyridinyl, piperidinyl, and piperazinyl urea compounds stimulate the release of acetylcholine and are thus useful analgesic agents for alleviating pain or as cholinergic agents which are useful for the amelioration of the symptoms of cognitive decline in the elderly.

These compounds have the general formula

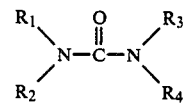

wherein $R_1$, $R_2$ and $R_4$ are phenyl or substituted phenyl, and $R_3$ is pyridinyl.

Pharmaceutical compositions including these compounds as well as methods for the preparation of the compounds are also disclosed.

25 Claims, No Drawings

TETRASUBSTITUTED UREA CHOLINERGIC AGENTS

BACKGROUND OF THE INVENTION

The present invention relates to compounds, pharmaceutical compositions, and to a pharmaceutical method of treatment. More particularly, this invention is concerned with a class of tetra-substituted urea compounds having cholinergic activity, with pharmaceutical compositions containing the compounds, and to a pharmaceutical method of treating the symptoms of disorders of cognition characterized by a cholinergic involvement, for example, cognitive decline in the elderly. These compounds, by virtue of their ability to enhance the release of acetylcholine, are also of interest because of their analgesic properties.

Disorders of cognition are generally characterized by symptoms of forgetfulness, confusion, memory loss, attentional deficits and/or, in some cases, affective disturbances. These symptoms may arise as a result of the general aging process and/or from organic brain disease, cerebrovascular disease, head injury or developmental or genetic defects.

The general decrease in cognitive function which accompanies the aging process is well accepted. The same phenomenon has been observed and documented in many lower mammals, including those routinely employed in pharmacological testing programs for screening and predicting usefulness for particular drugs in higher animals, including humans.

Although disorders of cognition often accompany the general aging process, presenile and senile primary degenerative dementia are the most common accepted causes of mental deterioration in the elderly. It has been estimated that at least ten percent of persons over sixty years of age will eventually suffer severe mental deterioration. A much larger number will experience cognitive decline of sufficient severity to impede their activities.

Many of the symptoms of cognitive disorders, especially impaired memory, are associated with decreased acetylcholine synthesis and the impairment of cholinoreceptive neurons. In the hippocampus and cerebral cortex of patients suffering from primary degenerative dementia for example, the level of the enzyme choline acetyltransferase (CAT) can be reduced by as much as ninety percent. (See Davies et al, *The Lancet*, 1976 (Vol. 2): 1403; Perry et al, *J. Neurol. Sci.*, 34: 247–265 (1977); and White et al, *The Lancet*, 1977 (Volume 1): 668–670)).

Since CAT catalyzes the synthesis of acetylcholine from its precursors choline and acetyl coenzyme A, the loss of CAT reflects the loss of cholinergic, or acetylcholine-releasing, nerve endings in the hippocampus and cerebral cortex. There is abundant evidence that cholinergic terminals in the hippocampus are critically important for memory formation.

The cholinergic hypothesis suggests that drugs which restore acety .choline levels, or which mimic the action of acetylcholine (i.e., are cholinomimetic) are effective in correcting this deficit in neurotransmitter chemical and provide treatment of the memory impairment symptom of cerebral insufficiency. Considerable biochemical, pharmacological, and electrophysiological evidence supports the hypothesis that deficits in the cholinergic system underlie geriatric cognitive dysfunction. (See C. Peterson and G. E. Gibson, *Neurobiol. Aging*, 4: 25–30 (1983)). Aged humans and nonhuman primates with decreased cognition show improved memory when they are treated, for example, with acetylcholinesterase inhibitors such as physostigmine. These agents increase the available supply of synaptic acetylcholine by inhibiting its hydrolysis.

Aminopyridines such as 3,4-diaminopyridine ameliorate age-related cognitive deficits by increasing the release of acetylcholine from presynaptic nerve terminals, thus increasing synaptic acetylcholine. (See H. P. Davis, et al, *Exp. Aging Res.*, 9: 211–214 (1983)).

It has been known for some time that the natural alkaloid muscarine has the ability to act relatively selectively at autonomic effector cells to produce qualitatively the same effects as acetylcholine. Two related alkaloids, pilocarpine and arecoline, have the same principal sites of action as muscarine and acetylcholine and are thus classified as having "muscarinic" action. Although these naturally occurring alkaloids are of great value as pharmacological tools, present clinical use is largely restricted to the use of pilocarpine as a miotic agent.

Arecoline (the methyl ester of 1,2,5,6-tetrahydro-1-methyl-3-pyridinecarboxylic acid) is the chief alkaloid found in betel nuts (*Areca catechu*). Betel nuts have been chewed by natives of the East Indies since early times as a euphoretic. The present pharmaceutical utility of arecoline, however, has been limited to its use as a veterinary anthelmintic agent.

Recently it has been demonstrated that arecoline is effective in ameliorating some of the symptoms of cognitive disorders in patients clinically diagnosed as having presenile primary degenerative dementia. Significant improvement was observed in a test of picture recognition after administration of arecoline to patients in a double blind study. (See Christie et al, *Brit. J. Psychiatry*, 138: 46–50 (1981)).

Regarding analgesia, the literature indicates that acetylcholine and muscarine agonists possess antinociceptive activity (see T. T. Chhau et al, *J. Pharmacol. Exp. Ther.*, 222: 612–666 (1982),; W. L. Dewey et al, *Life Sci.*, 17: 9–10 (1975); and N. W. Pedigo et al., *Neurosci. Lett.*, 26: 85–90 (1981) and references cited therein.)

SUMMARY OF THE INVENTION

In its broadest aspect, the present invention provides compounds having the structural formula

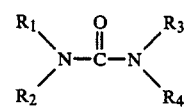

wherein $R_1$ and $R_2$ are each independently straight or branched alkyl of from one to four carbon atoms; cycloalkyl of from five to seven carbon atoms; phenyl; phenyl substituted with alkyl of from one to four carbon atoms, alkyloxy of from one to four carbon atoms, halogen, hydroxyl, nitro, trifluoromethyl, or $NR_5R_6$ where $R_5$ and $R_6$ are each independently hydrogen or alkyl of from one to four carbon atoms.

Alternatively, $R_1$ and $R_2$ when taken together with the nitrogen atom to which they are attached may form a ring denoted by

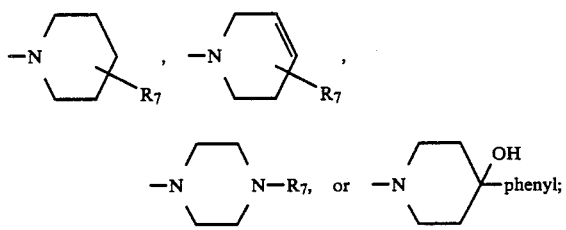

where R<sub>7</sub> is hydrogen; alkyl of from one to four carbon atoms; phenyl; 2-, 3-, or 4-pyridinyl; phenylalkyl of from seven to nine carbon atoms; or phenyl substituted with alkyl of from one to four carbon atoms, alkyloxy of from one to four carbon atoms, halogen, hydroxyl, nitro, trifluoromethyl, or NR$_5$R$_6$ where R$_5$ and R$_6$ are each independently hydrogen or alkyl of from one to four carbon atoms.

The substituent groups R$_3$ and R$_4$ are each independently phenyl; 2-, 3-, or 4-pyridinyl; or phenyl substituted with —SO$_2$—X, where X is hydroxyl, alkyloxy of from one to four carbon atoms, or NR$_5$R$_6$ where R$_5$ and R$_6$ are as defined above; alkyl of from one to four carbon atoms; alkyloxy of from one to four carbon atoms; alkoxycarbonyl of from two to five carbon atoms; halogen; hydroxyl; nitro; trifluoromethyl; or —NR$_5$R$_6$ where R$_5$ and R$_6$ are as defined above.

The present invention also includes pharmaceutically acceptable acid addition salts thereof.

In another aspect, the present invention provides pharmaceutical compositions useful in alleviating the symptoms of senile cognitive decline comprising an effective amount of a compound as described above in combination with a pharmaceutically acceptable carrier.

In yet another aspect, the present invention provides a method of alleviating the symptoms of cognitive decline in the elderly comprising administering to a patient in need of such treatment an effective amount of a pharmaceutical composition as defined above.

In another aspect, the present invention provides a method of alleviating pain in a mammal comprising administering to a mammal in need of such treatment an effective amount of a pharmaceutical composition as defined above.

DETAILED DESCRIPTION

The compounds of the present invention form a class of tetra-substituted derivatives of urea in which one nitrogen atom may be substituted with groups independently selected from alkyl of from one to four carbon atoms, cycloalkyl of from five to seven carbon atoms, and substituted or unsubstituted phenyl.

As used throughout this specification and the appended claims, the term "alkyl" denotes a straight or branched hydrocarbon group derived from an alkane by the removal of a single hydrogen atom as, for example, methyl, ethyl, propyl, isopropyl, n-, sec-, iso-, and tert-butyl, etc.

"Cycloalkyl of from five to seven carbon atoms" includes cyclopentyl, cyclohexyl, and cycloheptyl.

In another subgeneric aspect of the present invention, the groups R$_1$ and R$_2$ may join together with the nitrogen atom to which they are attached to form a piperazinyl ring which is substituted at the opposite ring-nitrogen atom with alkyl; phenyl; 2-, 3-, or 4-pyridinyl; phenylalkyl; or phenyl substituted with alkyl, alkyloxy, halogen, hydroxyl, nitro, amino, —SO$_3$H, —SO$_3$-alkyl (where alkyl contains from one to four carbon atoms), —SO$_2$NR$_5$R$_6$ (where R$_5$ and R$_6$ are independently hydrogen or alkyl of from one to four carbon atoms), trifluoromethyl, or dialkylamino.

As used throughout this specification and the appended claims, "alkyloxy" denotes an alkyl group, as defined above, attached to the parent molecular moiety through an oxygen atom.

"Halogen" means fluorine, chlorine, or bromine. The term "phenylalkyl" denotes a benzene ring, attached through a branched or unbranched alkyl group to the parent molecular moiety.

In another subgeneric aspect of the invention, the groups R$_1$ and R$_2$ may join together with the nitrogen atom to which they are attached to form a piperidinyl or 3,6-dihydro-1(2H)-pyridinyl ring, similarly substituted with alkyl; phenyl; 2-, 3-, or 4-pyridinyl; phenylalkyl; or phenyl substituted with alkyl, alkyloxy, halogen, hydroxyl, nitro, amino, —SO$_3$H, —SO$_3$-alkyl (where alkyl contains from one to four carbon atoms), —SO$_2$NR$_5$R$_6$ (where R$_5$ and R$_6$ are independently hydrogen or alkyl of from one to four carbon atoms), trifluoromethyl, or dialkylamino.

The substituent groups R$_3$ and R$_4$ of compounds of the invention are independently selected from 2-, 3-, or 4-pyridinyl; phenyl; and phenyl substituted with alkyl, phenyl, pyridinyl, phenylalkyl, or phenyl substituted with alkyl, alkyloxy, alkoxycarbonyl, halogen, hydroxyl, nitro, amino, —SO$_3$H, —SO$_3$-alkyl (where alkyl contains from one to four carbon atoms), —SO$_2$NR$_5$R$_6$ (where R$_5$ and R$_6$ are independently hydrogen or alkyl of from one to four carbon atoms), trifluoromethyl, or dialkylamino.

The term "alkoxycarbonyl" denotes

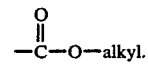

Compounds falling within the scope of the invention are exemplified by, but not limited to the following:

N,N-Dimethyl-N'-phenyl-N'-4-pyridinylurea.
N,N-Dimethyl-N'-(4-methylphenyl)-N'-4-pyridinylurea.
N-(3,4-Dichlorophenyl)-N',N'-dimethyl-N-(4-pyridinyl)urea.
N,N,-Dimethyl-N'-(3-nitrophenyl)-N'-4-pyridinylurea.
N-(4-Chloro-3-nitrophenyl)-N',N'-dimethyl-N-4-pyridinylurea.
N,N-Diethyl-N'-phenyl-N'-4-pyridinylurea.
N,N-bis(1-Methylethyl)-N'-phenyl-N'-4-pyridinylurea.
N,N-Dicyclohexyl-N'-(3,4-dichlorophenyl)-N'-4-pyridinylurea.
N-Methyl-N,N',N'-triphenylurea.
N,N,N'-Triphenyl-N'-2-pyridinylurea.
N,N,N'-Triphenyl-N'-4-pyridinylurea.
N-(3-Methylphenyl)-N',N'-diphenyl-N-4-pyridinylurea.
N-(4-Methylphenyl)-N',N'-diphenyl-N-(4-pyridinyl)urea.
N-(2-Chlorophenyl)-N',N'-diphenyl-N-(4-pyridinyl)urea.
N-(3-Chlorophenyl)-N',N'-diphenyl-N-4-pyridinylurea.
N-(4-Chlorophenyl)-N',N'-diphenyl-N-4-pyridinylurea.
N-(2,4-Dichlorophenyl)-N',N'-diphenyl-N-4-pyridinylurea.
N-(2-Nitrophenyl)-N',N'-diphenyl-N-4-pyridinylurea.

N-(3-Nitrophenyl)-N',N'-diphenyl-N-4-pyridinylurea.
N-(4-Chloro-3-nitrophenyl)-N',N'-diphenyl-N-4-pyridinylurea.
N,N-Diphenyl-N'-4-pyridinyl-N'-3-(trifluoromethyl)-phenyl]urea.
N,N-Diphenyl-N'-4-pyridinyl-N'-4-(trifluoromethyl)-phenyl]urea.
N-(3-Methoxyphenyl)-N',N'-diphenyl-N-4-pyridinylurea.
N'-(4-Methoxyphenyl)-N,N-diphenyl-N'-4-pyridinylurea.
2-[[(Diphenylamino)carbonyl]-4-pyridinylamino]benzoic acid, methyl ester.
N-3-(Dimethylamino)phenyl]-N',N'-diphenyl-N-4-pyridinylurea.
N,N-bis(4-Fluorophenyl)-N'-phenyl-N'-4-pyridinylurea.
N-(3-Chlorophenyl)-N',N'-bis(4-fluorophenyl)-N-(4-pyridinyl)urea.
N-(4-Chlorophenyl)-N',N'-bis(4-fluorophenyl)-N-4-pyridinylurea.
N-(3,4-Dichlorophenyl)-N',N'-bis(4-fluorophenyl)-N-4-pyridinylurea.
4-Methyl-N,N-diphenyl-1-piperazinecarboxamide.
N,N,4-Triphenyl-1-piperazinecarboxamide.
N,N-Diphenyl-4-(2-pyridinyl)-1-piperazinecarboxamide.
4-(2-Methylphenyl)-N,N-diphenyl-1-piperazinecarboxamide.
N,N-Dimethyl-4-(2-methylphenyl)-1-piperazinecarboxamide.
4-(3-Methylphenyl)-N,N-diphenyl-1-piperazinecarboxamide.
N,N-bis(4-Fluorophenyl)-4-(2-methylphenyl)-1-piperazinecarboxamide.
4-(2-Chlorophenyl)-N,N-diphenyl-1-piperazinecarboxamide.
4-(4-Chlorophenyl)-N,N-diphenyl-1-piperazinecarboxamide.
4-(2-Hydroxyphenyl)-N,N-diphenyl-1-piperazinecarboxamide.
4-(2-Methoxyphenyl)-N,N-diphenyl-1-piperazinecarboxamide.
N,N-Diphenyl-4-(phenylmethyl)-1-piperazinecarboxamide.
N-Phenyl-N-2-pyridinyl-4-(phenylmethyl)-1-piperazinecarboxamide.
N,N,4-Triphenyl-1-piperidinecarboxamide.
N,N-Diphenyl-4-(phenylmethyl)-1-piperidinecarboxamide.
4-(4-Chlorophenyl)-N,N-bis(4-fluorophenyl)-3,6-dihydro-1(2H)-pyridinecarboxamide.
3,6-Dihydro-N,N,4-triphenyl-1(2H)-pyridinecarboxamide.
4-(4-Chlorophenyl)-3,6-dihydro-N,N-diphenyl-(2H)-pyridinecarboxamide.
4-Hydroxy-N,N,4-triphenyl-1-piperidinecarboxamide.

The compounds of the present invention may be prepared by the methods detailed below in the Reaction Scheme and illustrated by preparative Examples 11, 18, 24, and 34 below. Specific preparative examples are given as illustrative of the general synthetic procedures employed.

The di-substituted amine compounds 1, where $R_1$ and $R_2$ are as defined above, are generally known compounds or, if not previously known, are synthesized by methods well known in the art. (See, for example, M. P. Sammes et al, *J. Chem. Soc. Perkin Trans.* 1, (5), 973–978 (1983) and earlier references cited therein.)

Reaction Scheme $$R_1\!\!\!\diagdown_{\!\!\!\diagup}\!\!N-H + Cl-\overset{O}{\overset{\|}{C}}-Cl \longrightarrow R_1\!\!\!\diagdown_{\!\!\!\diagup}\!\!N-\overset{O}{\overset{\|}{C}}-Cl +$$
$$1 \qquad \qquad \qquad 2$$

$$R_3\!\!\!\diagdown_{\!\!\!\diagup}\!\!N-H \longrightarrow R_1\!\!\!\diagdown_{\!\!\!\diagup}\!\!N-\overset{O}{\overset{\|}{C}}-N\!\!\!\diagup^{\!\!\!R_3}_{\!\!\!\diagdown R_4}$$
$$R_4 \qquad \qquad R_2$$
$$3$$

Compound 1 is converted to the corresponding di-substituted carbamic chloride, 2, by reaction with phosgene in an inert hydrocarbon solvent such as, for example, benzene, or toluene. The carbamic chloride compound, 2, is then reacted with the disubstituted amine compound 3, where $R_3$ and $R_4$ are as defined above, to produce the desired tetra-substituted urea compounds, 4. This reaction is generally carried out in an inert solvent such as chloroform in the presence of an acid scavenger such as triethylamine. The carbamic chloride compound is slowly added to a mixture of the disubstituted amine and, after addition is complete, the mixture is heated under reflux for a period of from twenty-four to seventy-two hours. The desired product is then separated from the reaction mixture and purified by conventional methods.

Compounds of the present invention where the $R_1$ and $R_2$ groups contain a basic nitrogen atom are capable of forming acid addition salts with pharmaceutically acceptable acids.

Examples of suitable acids for the formation of pharmaceutically acceptable salts of compounds of this invention are hydrochloric, sulfuric, phosphoric, acetic, benzoic, citric, malonic, salicylic, malic, fumaric, succinic, tartaric, lactic, gluconic, ascorbic, maleic, benzenesulfonic, methane- and ethanesulfonic, hydroxymethane- and hydroxyethanesulfonic, aspartic, and the like.

The salts are prepared by contacting the free base form of the compounds of this invention with a sufficient amount of the desired acid to produce the salt in the conventional manner. The free base forms may be regenerated, if desired, by treating the salt form with a base. For example, dilute aqueous solutions of such bases as sodium hydroxide, potassium carbonate, ammonia, and sodium bicarbonate may be utilized for this purpose.

Compounds of the present invention where one or more benzenesulfonic acid agroups are present are capable of forming salts with pharmaceutically acceptable, nontoxic bases. Suitable bases for salt formation include the hydroxides, carbonates, or bicarbonates of such metals as sodium, potassium, calcium, zinc, and iron. In addition, base addition salts may be formed by reaction with ammonium hydroxide or with pharmaceutically acceptable, nontoxic organic amines. Suitable amines for this purpose form a class well known to practitioners of the pharmaceutical arts. (See for example, Stephen M. Berg et al, *J. Pharm. Sci.*, 66: 1–19 (1977) which is incorporated herein by reference.) The salts are prepared by contacting the free benzenesulfonic acid form of the compounds with a sufficient amount of the desired base to produce the salt in the conventional manner. The free acid forms may be regenerated, if desired, by treating the salt form with an acid. For example, a dilute aqueous solution of hydrochloric acid may be utilized for this purpose.

The compounds of this invention act by stimulating the release of acetylcholine or, in some cases, by mimicking the action of cholinergic agents and are thus useful as agents for treating disorders of cognition characterized by a cholinergic involvement, for example cognitive decline in the elderly. The compounds of the present invention are also of interest as analgesic agents by virtue of their ability to enhance the release of acetylcholine.

The cholinergic activity of the compounds of the present invention was evaluated by determining the percent increase in spontaneous release or percent increase in potassium ion stimulated release of acetylcholine in the hippocampus of laboratory rats.

For the cholinergic system it has been shown that $^3$H-choline can be actively taken into the brain tissue by a sodium dependent high affinity choline uptake (HACU) system at concentrations lower than that of the HACU system and combine with acetyl CoA due to the action of choline acetyltransferase (CAT) to form $^3$H-ACh. This can then be released under depolarizing conditions (e.g. by the action of potassium ion) in the presence of $Ca^{+2}$.

Several representative compounds of the present invention were tested by this screening method, and the results appear in Table 1.

In Table 2, the data are presented for several representative compounds of this invention in the scopolamine-induced spontaneous swim test. Swimming activity of laboratory rats following the administration of the anticholinergic agent, scopolamine, has been found to be a rapid and reliable behavioral screen for compounds with cholinergic activity. The procedures for this test are basically a variation of those used to measure open field activity except that the animals must swim rather than run.

Untreated rats in this test will swim between 20 and 30 meters during a 5 minute test period. Rats given scopolamine at doses of 0.1 mg/kg develop a stereotypical swimming hyperactivity. Typically, the swimming distance increases 75-125% above baseline levels. This increase in activity associated with the administration of scopalomine is reversed by the administration of either the anticholine esterase, physostigmine, or a compound of the present invention.

The effect of scopalomine on swimming behavior has been determined to be centrally mediated since (1) the quaternary amine of scopolamine (scopolamine methyl nitrate) does not produce any behavioral change in this test and (2) the quaternary amine of physostigmine (neostigmine) does not reverse the effect of scopolamine.

TABLE 1

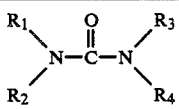

| | | | | Percent Increase Acetylcholine Release | |
|---|---|---|---|---|---|
| $R_1$ | $R_2$ | $R_3$ | $R_4$ | Spontaneous | $K^+$ Stimulated |
| | | | | (Molar conc. given in parentheses) | |
| Phenyl | Phenyl | Phenyl | 2-Pyridinyl | — | 150.8 ($10^{-4}$) |
| Phenyl | Phenyl | Phenyl | 4-Pyridinyl | — | 40.7 ($10^{-4}$) |
| Phenyl | Phenyl | 3-Methylphenyl | 4-Pyridinyl | 63.2 ($10^{-4}$) | — |
| Phenyl | Phenyl | 4-Methylphenyl | 4-Pyridinyl | 124.8 ($10^{-4}$) | — |
| Phenyl | Phenyl | 4-Chlorophenyl | 4-Pyridinyl | 59.2 ($10^{-4}$) | 58.1 ($10^{-4}$) |
| Phenyl | Phenyl | 2-Carboxymethylphenyl | 4-Pyridinyl | 41.8 ($10^{-4}$) | — |
| Phenyl | Phenyl | 3-Trifluoromethylphenyl | 4-Pyridinyl | 80.1 ($10^{-4}$) | — |
| Phenyl | Phenyl | 3-Dimethylaminophenyl | 4-Pyridinyl | 44.2 ($10^{-4}$) | — |
| 4-Fluorophenyl | 4-Fluorophenyl | 3-Chlorophenyl | 4-Pyridinyl | 132.2 ($10^{-4}$) | — |
| 4-Fluorophenyl | 4-Fluorophenyl | 4-Chlorophenyl | 4-Pyridinyl | 110.2 ($10^{-4}$) | — |
| 4-Fluorophenyl | 4-Fluorophenyl | 3,4-Dichlorophenyl | 4-Pyridinyl | 49.9 ($10^{-4}$) | — |
| 4-Phenylpiperidin-1-yl | | Phenyl | Phenyl | 17.2 ($10^{-4}$) | 66.8 ($10^{-4}$) |
| 4-Hydroxy-4-phenylpiperidin-1-yl | | Phenyl | Phenyl | — | 43.4 ($10^{-4}$) |
| 4-(2-Methylphenyl)piperazin-1-yl | | Phenyl | Phenyl | — | 104.2 ($10^{-5}$) |
| 4-(2-Methylphenyl)piperazin-1-yl | | 4-Fluorophenyl | 4-Fluorophenyl | 30.2 ($10^{-4}$) | 131.4 ($10^{-4}$) |
| 4-(Phenylmethyl)piperazin-1-yl | | Phenyl | 4-Pyridinyl | — | 67.0 ($10^{-4}$) |
| 4-(2-Chlorophenyl)piperazin-1-yl | | Phenyl | Phenyl | — | 114.8 ($10^{-4}$) |
| 4-(4-Chlorophenyl)piperazin-1-yl | | Phenyl | Phenyl | — | 57.7 ($10^{-4}$) |
| 4-(2-Methoxyphenyl)piperazin-1-yl | | Phenyl | Phenyl | — | 57.5 ($10^{-}$) |
| 4-(4-Chlorophenyl)-3,6-dihydro-1(2H)pyridin-1-yl | | 4-Fluorophenyl | 4-Fluorophenyl | — | 53.4 ($10^{-5}$) |
| Cyclohexyl | Cyclohexyl | 3,4-Dichlorophenyl | 4-Pyridinyl | 123.3 ($10^{-4}$) | — |
| 4-(2-Methylphenyl)piperazin-1-yl | | Cyclohexyl | Cyclohexyl | — | 36.95 ($10^{-4}$) |
| Phenyl | Phenyl | Phenyl | Phenyl | 44.3 ($10^{-4}$) | 51.8 ($10^{-4}$) |

TABLE 2

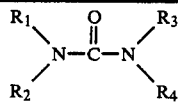

| R$_1$ | R$_2$ | R$_3$ | R$_4$ | \multicolumn{5}{c}{Percent Reversal of Scopolamine-Induced Swimming Activity at Various Doses (mg/kg)} |
|---|---|---|---|---|---|---|---|---|
| | | | | 0.32 | 1.0 | 3.2 | 1.0 | 32 |
| Phenyl | Phenyl | 3-Methylphenyl | 4-Pyridinyl | N (0%) | | C (28%) | | C (35%) |
| Phenyl | Phenyl | 4-Methylphenyl | 4-Pyridinyl | N (23%) | | A (54%) | | A (59%) |
| 4-(4-Chlorophenyl)-3,6-dihydro-1(2H)pyridin-1-yl | | 4-Fluorophenyl | 4-Fluorophenyl | | C (54%) | | C (43%) | |
| Methyl | Methyl | 3,4-Dichlorophenyl | 4-Pyridinyl | N (9%) | | N (25%) | | C (41%) |
| Methyl | Methyl | 4-Methylphenyl | 4-Pyridinyl | C (45%) | | C (39%) | | C (29%) |

A = Active - Reversal equal to control levels
C = Marginally active - Reversal not significantly different from control or scopolamine levels
N = Inactive - Reversal equal to scopolamine levels For preparing pharmaceutical compositions from the compounds of this invention, inert, pharmaceutically acceptable carriers can be either solid or liquid. Solid form preparations include powders, tablets, dispersable granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

For preparing suppositories, a low-melting wax such as a mixture of fatty acid glycerides and cocoa butter is first melted, and the active ingredient is dispersed therein by, for example, stirring. The molten homogeneous mixture is then poured into convenient sized molds and allowed to cool and solidify.

Powders and tablets preferably contain between about 5 to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid form preparations include solutions suitable for oral or parenteral administration, or suspensions, and emulsions suitable for oral administration. Sterile water solutions of the active component or sterile solutions of the active component in solvents comprising water, ethanol, or propylene glycol may be mentioned as examples of liquid preparations suitable for parenteral administration.

Sterile solutions may be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation in is unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

In therapeutic use as agents for treating cerebral insufficiency, the compounds utilized in the pharmaceutical method of this invention are administered to the patient at dosage levels of from 0.7 to 7000 mg per day. For a normal human adult of approximately 70 kg of body weight, this translates into a dosage of from 0.01 to 100 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

The following preparative examples are provided to enable one skilled in the art to practice the invention. They are illustrative of the methods employed to prepare the compounds listed in Table 3 and are not to be read as limiting the scope of the invention as it is defined by the appended claims.

EXAMPLE 11

Preparation of N,N,N'-triphenyl-N'-4-pyridinylurea

A solution of 8.51 g (0.05 mol) of N-phenyl-4-pyridinamine in 400 ml of chloroform is mixed with 11.5 g (0.11 mol) of triethylamine. To this mixture is added, dropwise with stirring, a solution of 11.6 G (0.05 mol) of diphenylcarbamic chloride in chloroform.

The mixture is then heated under reflux for 72 hours, cooled, and partitioned between water and chloroform. The combined chloroform extracts are dried over anhydrous magnesium sulfate and filtered. The filtrate is concentrated to an oil which is dissolved in diethyl ether, filtered, and washed with 2M NaOH and water. The ether solution is concentrated to give a solid which is recrystallized from ethyl acetate to yield N,N,N-triphenyl-N'-4-pyridinylurea, mp 156°–157° C.

EXAMPLE 18

Preparation of N-3,4-Dichlorophenyl-N',N'-diphenyl-N-4-pyridinylurea

Employing the general method of Example 11, 6.0 g (0.025 mol) of N-(3,4-dichlorophenyl)-4-pyridinamine, 2.6 g (0.025 mol) of triethylamine, and 5.8 g (0.025 mol) of diphenylaminocarbamic chloride in 150 ml of chloroform are heated under reflux for ten hours.

The crude reaction product is separated and purified by recrystallization to yield N-3,4-dichlorophenyl-N',N'-diphenyl-N-(4-pyridinylurea, mp 137°–141° C.

EXAMPLE 27

Preparation of N,N-bis-(4-Fluorophenyl)-N'-phenyl-N'-4-pyridinylurea (a) Preparation of bis-(4-fluorophenyl)carbamic chloride.

bis-(4-Fluorophenyl)amine (20.5 g, 0.10 mol) is dissolved, together with 0.13 mol of phosgene in benzene. After stirring this mixture for one hour at room temperature, the solution is heated under reflux overnight.

The solution is concentrated under vacuum to leave an oil which solidified upon cooling. The solid residue is recrystallized from cyclohexane to give 16.3 g of bis-(4-fluorophenyl)carbamic chloride, mp 53°–54° C.

(b) Preparation of N,N-bis-(4-fluorophenyl)-N'-phenyl-N'-4-pyridinylurea.

bis-(4-Fluorophenyl)carbamic chloride 5.35 g, 0.02 mol) is dissolved, together with 2.0 g of triethylamine in 100 ml of chloroform. To this mixture is added 3.4 g (0.02 mol) of N-phenyl-4-pyridinamine. The resulting mixture is heated under reflux for eight hours after which the solution is cooled to room temperature, washed three times with brine solution, dried, and evaporated.

The solid residue is recrystallized from diisopropyl ether to yield 4.5S g of N,N-bis-(4-fluorophenyl)-N'-phenyl-N'-4-pyridinylurea, mp 187°–191° C.

EXAMPLE 34

Preparation of 4-(3-Methylphenyl-N,N-diphenyl-1-piperazinecarboxamide

N-(3-Methylphenyl)piperazine hydrochloride (4.2 g, 0.017 mol, Aldrich Chemical Company, Milwaukee, Wisc., U.S.A.) is reacted with diphenylcarbamic chloride (3.9 g, 0.017 mol), together with 1.7 g (0.017 mol) of triethylamine in 100 ml of chloroform after the manner of Example 11.

Isolation and purification of the product by conventional methods gives 6.2 g of 4-(3-methylphenyl-N,N-diphenyl-1- piperazinecarboxamide, mp 119°–121°C.

Using the general methods of Examples 11, 18, 27, and 34 above, the compounds listed in Table 3 were prepared.

TABLE 3

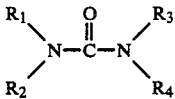

| EXAMPLE | R₁ | R₂ | R₃ | R₄ | M.p. °C. |
|---|---|---|---|---|---|
| 1 | Methyl | Methyl | Phenyl | 4-Pyridinyl | 89–93 |
| 2 | Methyl | Methyl | 4-Methylphenyl | 4-Pyridinyl | 107–108 |
| 3 | Methyl | Methyl | 3,4-Dichlorophenyl | 4-Pyridinyl | 117–120 |
| 4 | Methyl | Methyl | 3-Nitrophenyl | 4-Pyridinyl | 224–226* |
| 5 | Methyl | Methyl | 4-Chloro-3-nitrophenyl | 4-Pyridinyl | 127–130 |
| 6 | Ethyl | Ethyl | Phenyl | 4-Pyridinyl | 54–58 |
| 7 | 1-Methylethyl | 1-Methylethyl | Phenyl | 4-Pyridinyl | 153–155 |
| 8 | Cyclohexyl | Cyclohexyl | 3,4-Dichlorophenyl | 4-Pyridinyl | 140–142 |
| 9 | Methyl | Phenyl | Phenyl | Phenyl | 106–107 |
| 10 | Phenyl | Phenyl | Phenyl | 2-Pyridinyl | 197–201 |
| 11 | Phenyl | Phenyl | Phenyl | 4-Pyridinyl | 156–157 |
| 12 | Phenyl | Phenyl | 3-Methylphenyl | 4-Pyridinyl | 135–137 |
| 13 | Phenyl | Phenyl | 4-Methylphenyl | 4-Pyridinyl | 98–102 |
| 14 | Phenyl | Phenyl | 2-Chlorophenyl | 4-Pyridinyl | 140–143 |
| 15 | Phenyl | Phenyl | 3-Chlorophenyl | 4-Pyridinyl | 233–235* |
| 16 | Phenyl | Phenyl | 4-Chlorophenyl | 4-Pyridinyl | 149–150 |
| 17 | Phenyl | Phenyl | 2,4-Dichlorophenyl | 4-Pyridinyl | 115–120 |
| 18 | Phenyl | Phenyl | 3,4-Dichlorophenyl | 4-Pyridinyl | 137–141 |
| 19 | Phenyl | Phenyl | 2-Nitrophenyl | 4-Pyridinyl | 255–257* |
| 20 | Phenyl | Phenyl | 3-Nitrophenyl | 4-Pyridinyl | 161–164 |
| 21 | Phenyl | Phenyl | 4-Chloro-3-nitrophenyl | 4-Pyridinyl | 166–169 |
| 22 | Phenyl | Phenyl | 3-Trifluoromethylphenyl | 4-Pyridinyl | 103–106 |
| 23 | Phenyl | Phenyl | 4-Trifluoromethylphenyl | 4-Pyridinyl | 157–161 |
| 24 | Phenyl | Phenyl | 3-Methoxyphenyl | 4-Pyridinyl | 120–121 |

TABLE 3-continued

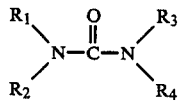

| EXAMPLE | R₁ | R₂ | R₃ | R₄ | M.p. °C. |
|---|---|---|---|---|---|
| 25 | Phenyl | Phenyl | 2-Methoxycarbonylphenyl | 4-Pyridinyl | 148–150 |
| 26 | Phenyl | Phenyl | 3-Dimethylaminophenyl | 4-Pyridinyl | 140–143 |
| 27 | 4-Fluorophenyl | 4-Fluorophenyl | Phenyl | 4-Pyridinyl | 187–191 |
| 28 | 4-Fluorophenyl | 4-Fluorophenyl | 3-Chlorophenyl | 4-Pyridinyl | 166–168 |
| 29 | 4-Fluorophenyl | 4-Fluorophenyl | 4-Chlorophenyl | 4-Pyridinyl | 174–178 |
| 30 | 4-Methylpiperazin-1-yl | | Phenyl | Phenyl | 194* |
| 31 | 4-Phenylpiperazin-1-yl | | Phenyl | Phenyl | 111.5–112-5 |
| 32 | 4-(2-Pyridinyl)piperazin-1-yl | | Phenyl | Phenyl | 143–144 |
| 33 | 4-(2-Methylphenyl)piperazin-1-yl | | Phenyl | Phenyl | 158–161 |
| 34 | 4-(3-Methylphenyl)piperazin-1-yl | | Phenyl | Phenyl | 119–121 |
| 35 | 4-(2-Methylphenyl)piperazin-1-yl | | 4-Fluorophenyl | 4-Fluorophenyl | 201–203 |
| 36 | 4-(2-Chlorophenyl)piperazin-1-yl | | Phenyl | Phenyl | 188–189 |
| 37 | 4-(4-Chlorophenyl)piperazin-1-yl | | Phenyl | Phenyl | 177.5–178.5 |
| 38 | 4-(2-Hydroxyphenyl)piperazin-1-yl | | Phenyl | Phenyl | 136–138 |
| 39 | 4-(2-Methoxyphenyl)piperazin-1-yl | | Phenyl | Phenyl | 174–175 |
| 40 | 4-(Phenylmethyl)piperazin-1-yl | | Phenyl | Phenyl | 80–81 |
| 41 | 4-(Phenylmethyl)piperazin-1-yl | | Phenyl | 2-Pyridinyl | 120–122 |
| 42 | 4-Phenylpiperidin-1-yl | | Phenyl | Phenyl | 134–135 |
| 43 | 4-Phenylmethylpiperidin-1-yl | | Phenyl | Phenyl | 119–120 |
| 44 | 4-(Phenyl)-3,6-dihydro-1(2H)pyridin-1-yl | | Phenyl | Phenyl | 140–141 |
| 45 | 4-(4-Chlorophenyl)-3,6-dihydro-1(2H)pyridin-1-yl | | Phenyl | Phenyl | 177–178 |
| 46 | 4-(4-Chlorophenyl)-3,6-dihydro-1(2H)pyridin-1-yl | | 4-Fluorophenyl | 4-Fluorophenyl | 126–127 |
| 47 | 4-Hydroxy-4-phenyl-piperidin-1-yl | | Phenyl | Phenyl | 188–189 |

*This is the melting point of the hydrochloride salt.

We claim:
1. A compound having the formula

$$\begin{array}{c} R_1 \\ \diagdown \\ R_2 \end{array} N - \overset{\overset{\displaystyle O}{\|}}{C} - N \begin{array}{c} \diagup R_3 \\ \diagdown R_4 \end{array}$$

wherein R₁ and R₂ are each independently
phenyl;
phenyl substituted with
 alkyl of from one to four carbon atoms,
 alkyloxy of from one to four carbon atoms,
 halogen,
 hydroxyl,
 nitro,
 trifluoromethyl, or
 —NR₅R₆ where R₅ and R₆ are independently hydrogen or alkyl of from one to four carbon atoms;
wherein R₃ is 2-, 3-, or 4-pyridinyl and R₄ is
phenyl; or
phenyl substituted with
 alkyl of from one to four carbon atoms,
 alkyloxy of from one to four carbon atoms,
 alkoxycarboyl of from two or five carbon atoms,
 halogen,
 hydroxy,
 nitro,
 trifluoromethyl, or
 —NR₅R₆ where R₅ and R₆ are as defined above;
or a pharmaceutically acceptable salt thereof.

2. A compound as defined in claim 1 having the name N,N,N'-triphenyl-N'-2-pyridinylurea or a pharmaceutically acceptable salt thereof.

3. A compound as defined in claim 1 having the name N,N,N'-triphenyl-N'-4-pyridinylurea or a pharmaceutically acceptable salt thereof.

4. A compound as defined in claim 1 having the name N-(3-methylphenyl)-N',N'-diphenyl-N-4-pyridinylurea or a pharmaceutically acceptable salt thereof.

5. A compound as defined in claim 1 having the name N-(4-methylphenyl)-N',N'-diphenyl-N-(4-pyridinyl)urea or a pharmaceutically acceptable salt thereof.

6. A compound as defined in claim 1 having the name N-(2-chlorophenyl)-N',N'-diphenyl-N-(4-pyridinyl)urea or a pharmaceutically acceptable salt thereof.

7. A compound as defined in claim 1 having the name N-(3-chlorophenyl)-N',N'-diphenyl-N-4-pyridinylurea or a pharmaceutically acceptable salt thereof.

8. A compound as defined in claim 1 having the name N-(4-chlorophenyl)-N',N'-diphenyl-N-4-pyridinylurea or a pharmaceutically acceptable salt thereof.

9. A compound as defined in claim 1 having the name N-(2,4-dichlorophenyl)-N',N'-diphenyl-N-4-pyridinylurea or a pharmaceutically acceptable salt thereof.

10. A compound as defined in claim 1 having the name N-(2-nitrophenyl)-N',N'-diphenyl-N-4-pyridinylurea or a pharmaceutically acceptable salt thereof.

11. A compound as defined in claim 1 having the name N-(3-nitrophenyl)-N',N'-diphenyl-N-4-pyridinylurea or a pharmaceutically acceptable salt thereof.

12. A compound as defined in claim 1 having the name N-(4-chloro-3-nitrophenyl)-N',N'-diphenyl-N-4-pyridinylurea or a pharmaceutically acceptable salt thereof.

13. A compound as defined in claim 1 having the name N,N-diphenyl-N'-4-pyridinyl-N'-[3-(trifluoromethyl)phenyl]urea or a pharmaceutically acceptable salt thereof.

14. A compound as defined in claim 1 having the name N,N-diphenyl-N'-4-pyridinyl-N'-4-(trifluoromethyl)phenyl]urea or a pharmaceutically acceptable salt thereof.

15. A compound as defined in claim 1 having the name N-(3-methoxyphenyl)-N',N'-diphenyl-N-4-pyridinylurea or a pharmaceutically acceptable salt thereof.

16. A compound as defined in claim 1 having the name N'-(4-methoxyphenyl)-N,N-diphenyl-N'-4-pyridinylurea or a pharmaceutically acceptable salt thereof.

17. A compound as defined in claim 1 having the name N-[3-(dimethylamino)phenyl]-N',N'-diphenyl-N-4-pyridinylurea or a pharmaceutically acceptable salt thereof.

18. A compound as defined in claim 1 having the name N,N-bis(4-fluorophenyl)-N'-phenyl-N'-4-pyridinylurea or a pharmaceutically acceptable salt thereof.

19. A compound as defined in claim 1 having the name N-(3-chlorophenyl)-N',N'-bis(4-fluorophenyl)-N-4-pyridinylurea or a pharmaceutically acceptable salt thereof.

20. A compound as defined in claim 1 having the name N-(4-chlorophenyl)-N',N'-bis(4-fluorophenyl)-N-4-pyridinylurea or a pharmaceutically acceptable salt thereof.

21. A compound as defined in claim 1 having the name N-(3,4-dichlorophenyl)-N',N'-bis(4-fluorophenyl)-N-4-pyridinylurea or a pharmaceutically acceptable salt thereof.

22. A pharmaceutical composition for alleviating pain in a mammal comprising an analgesically effective amount of a compound as defined by claim 1 together with a pharmaceutically acceptable carrier.

23. A pharmaceutical composition for treating the symptoms of cognitive decline in the elderly comprising an effective amount of a compound as defined in claim 1 in combination with a pharmaceutically acceptable carrier.

24. A method of alleviating pain in a mammal comprising administering to a mammal in need of such treatment an analgesically effective amount of a compound in accordance with claim 1 together with a pharmaceutically acceptable carrier.

25. A method of treating the symptoms of cognitive decline in the elderly comprising administering an effective amount of a compound as defined in claim 1 in combination with a pharmaceutically acceptable carrier.

* * * * *